United States Patent [19]

Hausler et al.

[11] Patent Number: 4,667,150
[45] Date of Patent: May 19, 1987

[54] MULTIELECTRODE PROBE AND CIRCUITRY AND PROCESS PERTAINING THERETO

[75] Inventors: Rudolph H. Hausler, Des Peres; Allen L. Savage, St. Louis, both of Mo.; Jack B. Harrell, Jr., Friendswood, Tex.

[73] Assignee: Petrolite Corporation, St. Louis, Mo.

[21] Appl. No.: 786,708

[22] Filed: Oct. 11, 1985

Related U.S. Application Data

[63] Continuation of Ser. No. 401,166, Jul. 23, 1982, abandoned.

[51] Int. Cl.⁴ ............................................. G01N 27/46
[52] U.S. Cl. .................................. 324/65 CR; 204/1 T
[58] Field of Search ............... 204/1 T, 1 C, 195 C, 204/129.2; 324/65 CR

[56] References Cited

U.S. PATENT DOCUMENTS

| | | | |
|---|---|---|---|
| 3,358,229 | 12/1967 | Collins | 324/65 CR |
| 3,406,101 | 10/1968 | Kilpatrick . | |
| 3,418,848 | 12/1968 | Schaschl | 324/65 CR |
| 3,436,320 | 4/1969 | Marsh | 324/65 CR |
| 3,631,338 | 12/1971 | Fitzpatrick . | |
| 3,943,488 | 3/1976 | Kazahaya | 340/825.03 |
| 3,996,124 | 12/1976 | Eaton | 324/65 CR |
| 4,049,525 | 9/1977 | Dutton . | |
| 4,102,769 | 7/1978 | Seyl | 324/65 CR |
| 4,226,693 | 10/1980 | Maes | 324/65 CR |
| 4,454,006 | 6/1984 | Hausler | 324/65 CR X |

FOREIGN PATENT DOCUMENTS

| | | | |
|---|---|---|---|
| 868012 | 4/1971 | Canada . | |
| 881095 | 9/1971 | Canada . | |
| 920664 | 2/1973 | Canada . | |
| 2252442 | 9/1979 | Fed. Rep. of Germany . | |
| 1263219 | 2/1972 | United Kingdom | 324/65 CR |
| 0724991 | 3/1980 | U.S.S.R. | 324/65 CR |

*Primary Examiner*—Reinhard J. Eisenzopf
*Assistant Examiner*—Jose M. Solis
*Attorney, Agent, or Firm*—Pravel, Gambrell, Hewitt & Kimball

[57] ABSTRACT

A system, method and probe for monitoring the corrosion rate of different metals in identical corrosive fluids and under identical conditions, such metals being employed as electrodes other than reference electrodes in a probe having also a reference electrode. The preferred probe comprises a probe body holding at least four electrodes, where one is placed in the center and the others around it in a circle. The center electrode is preferably used as a permanent reference electrode. Each electrode on the circle can then be connected in turn to a channel on a multistation PAIR meter as test and auxiliary electrodes, whereby the corrosion rate on each of them can be monitored in turn. This arrangement greatly enhances the utility of the multistation PAIR meter and with only two entry ports in a system, all channels can serve to answer specific questions on specific electrodes or metals. The novel probe can also be used with a one channel PAIR meter employed with a multi-station manual switch.

In an alternative electrode arrangement, the center electrode is used as a permanent auxiliary electrode while the system itself is used as a reference electrode and a plurality of test electrodes are employed.

8 Claims, 5 Drawing Figures

MULTIELECTRODE PROBE AND CIRCUITRY AND PROCESS PERTAINING THERETO

This is a continuation of co-pending application Ser. No. 401,166 filed on July 23, 1982, now abandoned.

BACKGROUND AND OBJECTS OF THE INVENTION

This invention relates to measuring corrosion and it relates more particularly to instruments and techniques used in the study of corrosion processes, and most particularly to the monitoring of corrosion rates on a number of different metals and for various galvanic situations, preferably under actual process conditions.

Industrial plants, as well as oil field equipment, are built from many different structural and functional metals, and often a multitude of these are in contact with the aggressive fluids. It has been assumed in the past that the corrosion rates of these different metals (in particular, the different steels) can be adequately represented by a single test specimen such as AISI-1018 steel. This assumption is incorrect for several reasons:

(a) It has been observed that pitting rates on these different steels are entirely different.

(b) The response to inhibitors of different metals is often quite different. For instance, it has been observed that the corrosion of SA-533A steel increases much faster at marginal corrosion inhibitor concentrations than the corrosion rate for AISI-1018 or ASTM-285C.

(c) Different metals respond differently to process upsets (in chemical cleaning studies it has been found, for instance, that ASTM-533A alloy corrosion is accelerated much less in the presence of oxygen or under oxidizing conditions than AISI-1018 carbon steel.)

(d) Galvanic coupling of metals is unavoidable and different metals again respond differently to such effects.

It is therefore, essential to monitor corrosion rates on a number of different metals and for various galvanic situations as well as under actual process conditions. Such monitoring may be concerned with general corrosion rates, pitting corrosion, adequate protection by inhibitors or for the purpose of determining process upsets. The purpose of such monitoring, of course, is aimed at failure prediction and proper maintenance outage scheduling.

Corrosion rates can be conveniently monitored by the linear polarization technique such as is carried out with the PAIR instruments and probes available from the Petreco Division of the Petrolite Corporation. A PAIR instrument is described and claimed in U.S. Pat. No. 3,406,101, issued Oct. 15, 1968 to James W. Kilpatrick, the disclosure of which is hereby incorporated by reference. The PAIR technique employs three electrodes on an electrode holder, of which one is the test electrode (cathode), another one used as auxiliary electrode (anode) and the third as reference electrode. This technique, therefore, requires one entry port in order to attain one data point. Furthermore, it has been assumed in the past that the linear polarization technique is only adequate for general corrosion rate monitoring while a zero resistance ammeter is necessary to monitor galvanic current situations. Therefore, the current state of the art requires several instruments and a multitude of entry ports into an actual system in order to monitor corrosion on different metals and for galvanic situations.

The objects of this invention are to provide instrumentation, circuitry and a method to enable this complex monitoring task to be simplified.

Other objects of the invention will be apparent from the following description of the invention.

SUMMARY OF THE INVENTION

The above and other objects of the invention may be accomplished by providing a novel multi-electrode probe for use in measuring corrosion rates, circuit means for connecting such probe to a corrosion rate measuring instrument, and a method for monitoring the corrosion rate of different metals in identical corrosive fluids and under identical conditions, employing such probe and circuit means.

The novel probe of this invention comprises electrode holding means; a first rod-shaped metallic electrode held by the holding means and extending outwardly from and centrally positioned with respect thereto; at least three other rod-shaped metallic electrodes of differing composition also held by and extending outwardly from the holding means and arranged symmetrically in a circle around the first electrode, all the electrodes being parallel to each other; means for insulating and sealing the electrodes in a fluid tight manner from the holding means; electrical terminal means on the holding means; and conductive means in the holding means for connecting each of the electrodes to a respective terminal means. The electrodes are preferably cylindrical.

The centrally positioned electrode is preferably used as a reference electrode, with each of the other electrodes being adapted for use either as a test or an auxiliary electrode. Alternatively, the centrally positioned electrode may serve as a permanent auxiliary electrode, with the other electrodes being test electrodes. In that embodiment, the system is used as a reference electrode, e.g., the holding means being adapted for such purpose.

At least one of the test or test/auxiliary electrodes may be a galvanically coupled electrode comprising two dimensionally substantially identical metallic rods, differing in composition, which are electrically connected by conductive means which also serves to hold the two rods in end to end relationship, fluid tight sealing means being positioned between the rods and at the end of the electrode opposite the holding means. Such galvanically coupled electrodes are disclosed and claimed in U.S. Pat. No. 4,454,006 issued June 12, 1984, the disclosure of which is hereby incorporated by reference.

The invention also includes circuit means for connecting a probe of the preferred type, i.e., with a center reference electrode, as above described, to a corrosion rate measuring instrument having one or more channels, each channel being provided with terminal means, each terminal means including terminals for connection to electrodes serving as reference, test and auxiliary electrodes, respectively. With a multi-channel instrument, such ciruict means comprises: conductive means including parallel branches connecting the reference electrode with the reference electrode terminal in each terminal means; and conductive means including parallel branches connecting each electrode other than the reference electrode to a test electrode terminal in one terminal means and an auxiliary electrode terminal in a different terminal means, each terminal being connected to only a single electrode.

Where the instrument is of the single channel variety, the connecting circuit comprises: first and second multiple pole switching means, each having a plurality of stationary poles and a common terminal mounting a movable contactor; conductive means for connecting the common terminals of the first and second switching means with the test and auxiliary electrode terminals respectively, of the measuring instrument; conductive means including parallel branches for connecting each electrode other than the reference electrode to a pole of each of the first and second switching means, each pole being connected to only a single electrode; and conductive means for mechanically interlocking said first and second switching means so that the two contactors move synchronously in a fixed sequence.

The invention further includes a system and method for monitoring the corrosion rate of different metals in identical corrosive fluids and under identical conditions, such metals being employed as electrodes other than reference electrodes in a probe having also a reference electrode. The system comprises in combination, a corrosion rate probe having a reference electrode and a plurality of electrodes other than reference electrodes; a corrosion rate measuring instrument having one or more channels, each provided with terminal means including terminals for connection to electrodes serving as reference, test and auxiliary electrodes, respectively; means for connecting each electrode other than the reference electrode in sequence to a channel in the measuring instrument and, where a dedicated auxiliary electrode is not employed, first as a test electrode and then as an auxiliary electrode; and means for connecting the reference electrode with the reference electrode terminal of the measuring instrument. Where the measuring instrument has multiple channels, each channel is adapted to be activated in turn to monitor a different electrode serving as a test electrode. Where a single channel instrument is used, the system includes switching means for accomplishing the connection sequence.

The method comprises: (a) immersing the electrodes in the corrosive fluid; (b) allowing them to remain in the fluid for a period of undisturbed corrosion; and (c) connecting each electrode other than the reference electrode in turn to a channel in a corrosion rate measuring instrument, and, where a dedicated auxiliary electrode is not employed, first as a test electrode and then as an auxiliary electrode. The corrosion rate measuring instrument may have multiple channels with each channel being activated in turn to monitor a different electrode serving as a test electrode; or may be a single channel instrument, the connection sequence being accomplished by switching means.

DETAILED DESCRIPTION OF THE INVENTION

Figure 2:
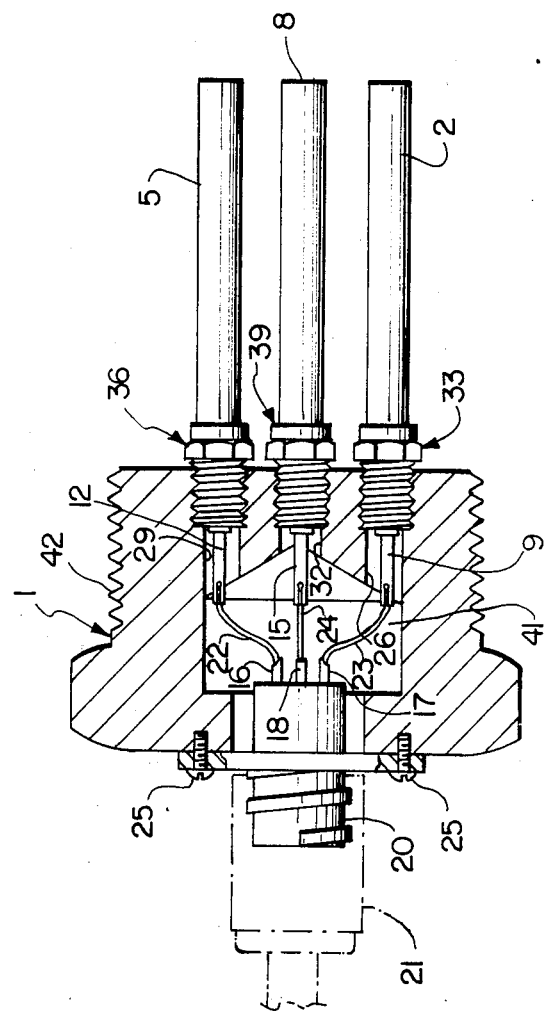
FIG. 2 is a view, partly in section, taken along line 2—2 of the probe assembly shown in FIG. 1.
Figure 1:
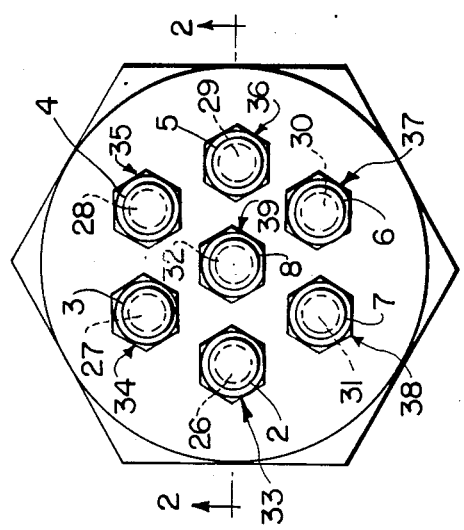
FIG. 1 is a bottom (fluid-side) view of the probe assembly of this invention.

Referring to FIGS. 1 and 2, there is shown a probe assembly which comprises a metallic body 1, on which are carried replaceable cylindrical electrodes 2, 3, 4, 5, 6, 7 and 8, of which electrode 8 is a reference electrode and the remaining electrodes are of varying composition and serve in turn as test and auxiliary electrodes. These electrodes extend outwardly from probe body 1 and are parallel to each other. Reference electrode 8 is centrally positioned with respect to probe body 1 and the other electrodes are arranged symmetrically in a circle around the reference electrode. FIG. 2 shows three of these electrodes, namely electrodes 2, 5 and 8. These electrodes are secured by threaded or other means, not shown, to metallic pins 9, 12 and 15, respectively, which in turn are connected within the body 1 by insulated electrically conductive means 22, 23 and 24, respectively, to the respective terminal lugs, 16, 17 and 18 of a multi-connector electrical fitting 20 carried on top of body 1. Lugs 16, 17 and 18 are electrically common to respective pins, not shown, of multipin fitting 20, secured to the top of probe body 1 by screws 25. Electrical connection to a multi-channel corrosion rate monitoring instrument such as the Petrolite Corporation's Model 1010 ten-channel PAIR meter is by a cable connector 21, carrying conductors connected respectively to the pins of fitting 20. Such conductors may be as shown in U.S. Pat. No. 3,639,876, issued Feb. 1, 1972 to Homer M. Wilson, the disclosure of which in this and other respects is hereby incorporated by reference. However, any insulated conductive means may be used for this purpose, including Conax connectors with special insulating glands, which are particularly useful for high temperature and high pressure applications. Electrodes 3, 4, 6 and 7, not shown in FIG. 2, are similarly secured and connected with conductors in cable connector 32. The conductors are shown schematically in the circuit diagram of FIG. 3 as 72, 73, 74, 75, 76, 77 and 59.

Probe body 1 carries external threads 24 which are adapted to engage with interior threads of a pipe fitting which forms part of a piping system carrying fluids whose corrosive effect it is desired to determine, as shown in U.S. Pat. No. 3,639,876. A cavity 41, preferably cylindrical, as shown, is provided from the top of the body 1 to a region adjacent the lower cylindrical portion carrying threads 42. The lower portion of the body 1 is provided with a plurality of passageways 26, 27, 28, 29, 30, 31 and 32. These passageways are threaded, at least in part, to receive insulating members 33, 34, 35, 36, 37, 38 and 39 through which pass metallic pins, of which three, namely 9, 12 and 15, passing through members 33, 36 and 39, respectively, are shown in FIG. 2. Insulating members 33, 34, 35, 36, 37, 38 and 39, which include fluid tight sealing means, may be of the construction shown in U.S. Pat. No. 3,639,876. The ends of the pins 9, 12 and 15 extend within the cavity 41 and are provided with threads or other attaching surfaces, not shown, onto which electrical connections may be made. More particularly, electrical conductors 9, 10, 11, 12, 13, 14 and 15 are secured to the attaching surfaces of the pins by terminal clips or equivalent means, not shown. Further details with respect to the electrodes, pins, insulating and sealing means, etc., are like those shown in U.S. Pat. No. 3,639,876.

Figure 5:
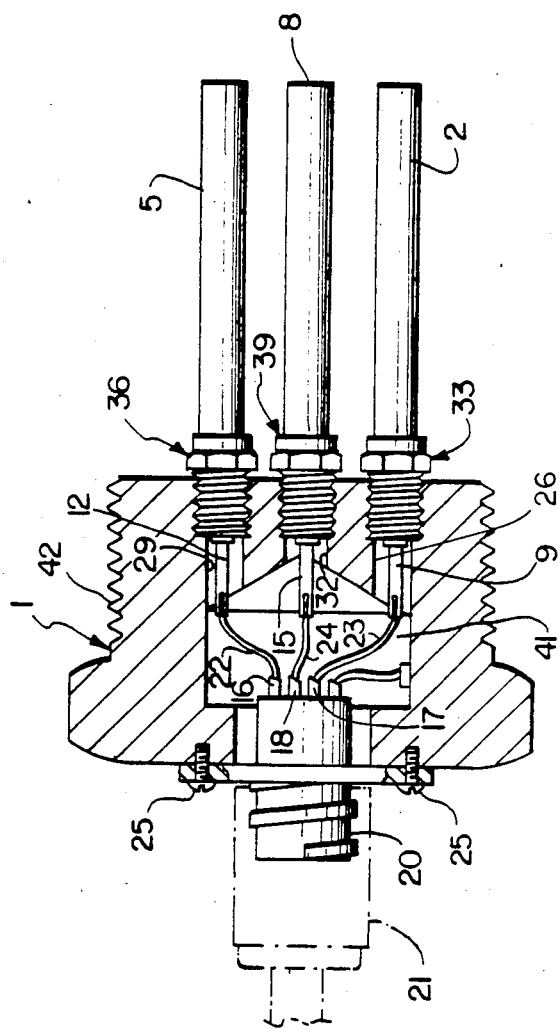
FIG. 5 is a view, partly in section, of a probe assembly having the holding means used as an electrode.

Although the probe as described above has the reference electrode in the center and the other electrodes arranged around it in a circle, alternative arrangements are, of course, possible, e.g., where the center electrode could be used as a permanent auxiliary electrode and the system itself is used as a reference electrode FIG. 5.

Moreover, one or more of the test or test/auxiliary electrodes may be a galvanically coupled electrode comprising two dimensionally substantially identical metallic rods, differing in composition, which are electrically connected to conductive means which also serves to hold the two rods in end to end relationship, fluid tight sealing means being positioned between the rods and at the end of the electrode opposite the holding means, as described and claimed in U.S. Pat. No. 4,454,006.

It will be apparent that the multi-electrode probe of this invention is not restricted to the details of any particular probe holder or assembly, such as that above described, but extends to any holder suitable for holding three or more electrodes in a circular arrangement around a central electrode, with any suitable insulation and sealing means. Moreover, as above indicated, the probe may be one using the body of the probe itself, i.e., the holder, as the reference electrode and having a plurality of test electrodes which can be used in turn, along with a permanent auxiliary electrode which may be centrally positioned.

The present multi-electrode may, by employing a multistation manual switch, be used with a single channel corrosion rate measuring instrument, preferably one based on linear polarization and using a three electrode probe, such as the Petrolite Model M 103 PAIR meter. However, the multi-electrode probe is particularly useful with, and greatly enhances the utility of, a multichannel meter such as the Petrolite Corporation Model 1010 ten channel meter, when used in association with it. With the use of such an arrangement and with only two entry parts in a system, all channels can serve to answer specific questions on specific electrodes or metals.

Figure 3:
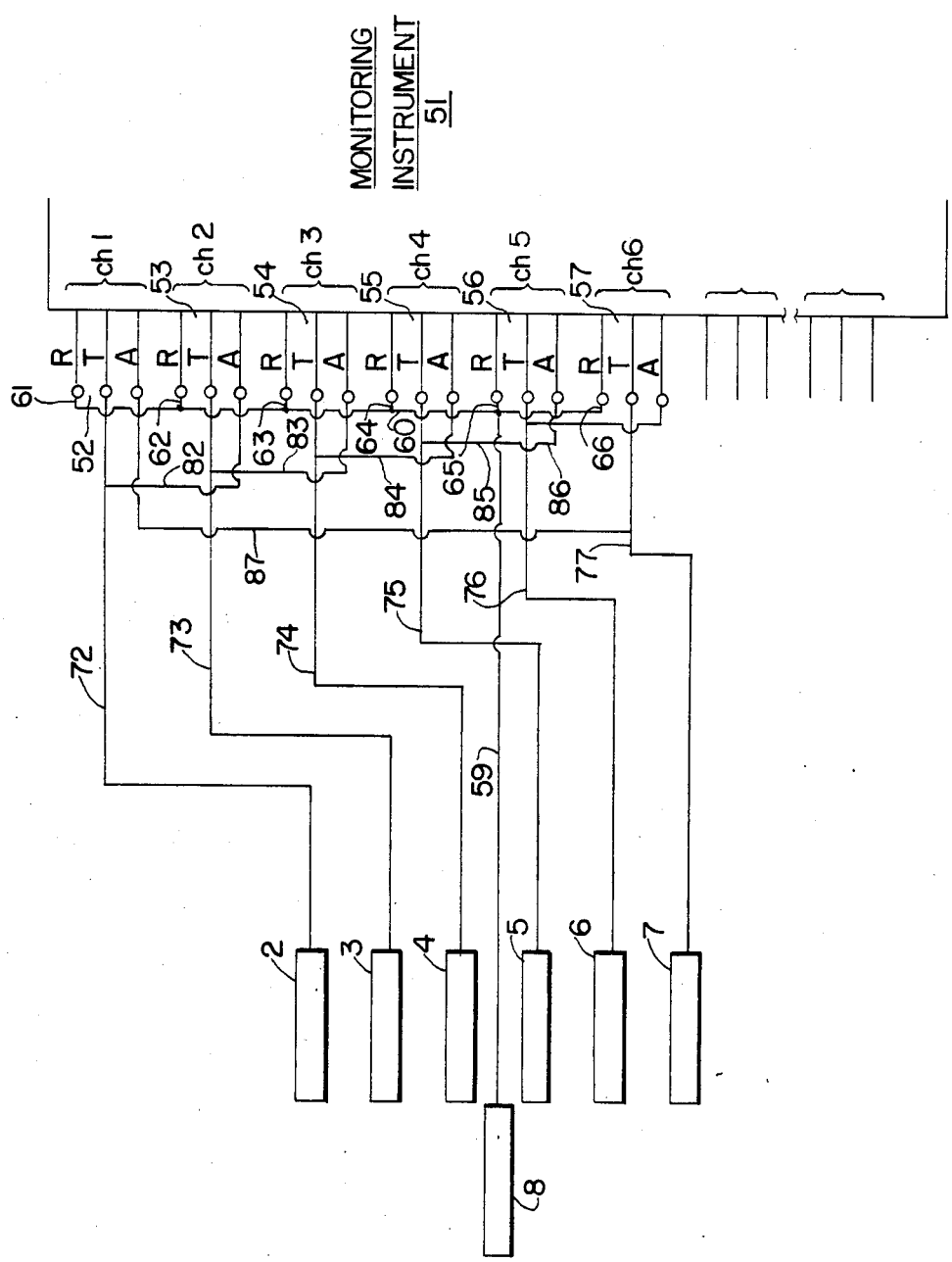
FIG. 3 is a circuit diagram illustrating the connection of seven electrodes from a probe assembly as shown in FIGS. 1 and 2 to a multichannel corrosion rate monitoring instrument intended for use with three electrode probes.

The circuit diagram of FIG. 3 illustrates the circuit contemplated for connecting the probe shown in FIGS. 1 and 2 with a multichannel corrosion rate monitoring instrument, preferably one based on linear polarization and intended for a three electrode probe, such as the Petrolite Corporation's Model 1010 PAIR meter, designated generally as 51. It will be seen that six channels of the PAIR meter are utilized, each provided with terminal means designated 52, 53, 54, 55, 56 and 57, respectively. Each terminal means includes terminals for connection to electrodes employed as reference, test and auxiliary electrode, labelled R, T and A, respectively. The reference electrode 8 of the probe is connected by means of conductors 59 and 60 and branching conductors 61, 62, 63, 64, 65 and 66 to the terminals 52R, 53R, 54R and 57R, respectively. Electrodes 2, 3, 4, 5, 6 and 7 are connected by means of conductors 72, 73, 74, 75, 76 and 77, respectively, to terminals 52T, 53T, 54T, 55T, 56T and 57T respectively. Branching conductors 82, 83, 84, 85, 86 and 87 are connected with conductors 72, 73, 74, 75, 76 and 77, respectively, and are connected at their other ends with terminals 53A, 54A, 55A, 57A, and 52A, respectively. Thus, each of the non-reference electrodes 2, 3, 4, 5, 6 and 7 may be used in sequence as a test, then auxiliary electrode, with the result that the corrosion rate on each of these electrodes can be monitored in turn.

Figure 4:
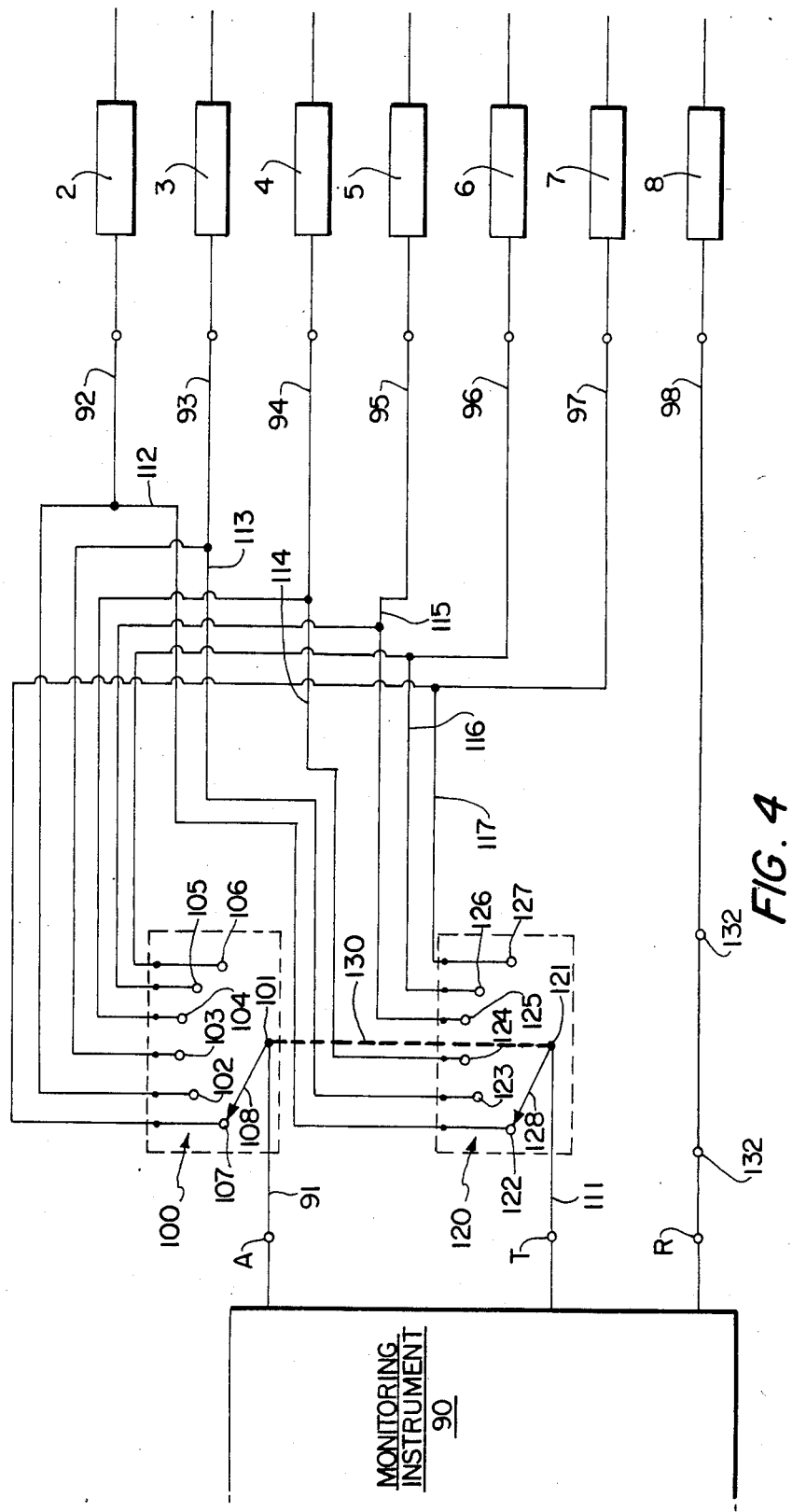
FIG. 4 is a circuit diagram illustrating the connection of seven electrodes from a probe assembly as shown in FIGS. 1 and 2 to a single channel corrosion rate monitoring instrument intended for use with three electrode probes.

Referring to FIG. 4, there is illustrated a circuit for connecting the probe shown in FIGS. 1 and 2 with a single channel corrosion rate monitoring instrument, preferably one based on linear polarization and intended for a three electrode probe, such as Petrolite Corporation's Model M 103 PAIR meter, designated generally as 90 and having terminals for connection to electrodes employed as reference, test and auxiliary electrode, labelled R, T and A, respectively. Electrodes 2, 3, 4, 5, 6 and 7 of the probe are connected by means of conductors 92, 93, 94, 95, 96 and 97, respectively, to poles 102, 103, 104, 105, 106 and 107 of a first multipole rotary switch designated generally as 100. Branching conductors 112, 113, 114, 115, 116 and 117 are conducted with conductors 92, 93, 94, 95, 96 and 97, respectively, and are connected at their other ends with poles 122, 123, 124, 125, 126 and 127 of a second multipole rotary switch designated generally as 120. The common terminal 101 of the switch 100 is connected by means of conductor 91 to the auxiliary electrode terminal A of the monitoring instrument 90. Similarly, the common terminal 121 of switch 120 is connected by means of conductor 111 to the test electrode terminal T of the monitoring instrument 90. Switches 100 and 120 are mechanically interlocked by conventional means shown schematically by dash line 130 so that the switch contactors 108 and 128, mounted on common terminals 101 and 121, respectively, move synchronously in a fixed sequence. Reference electrode 8 of the probe is connected via conductive means 98, which may include terminals 132 and 133 associated with the switching means, with the reference electrode terminal R of the monitoring instrument 90. Thus (as in the case of the circuit shown in FIG. 3), each of the nonreference electrodes 2, 3, 4, 5, 6 and 7 may be used in sequence as a test, then auxiliary electrode, with the result that the corrosion rate on each of these electrodes can be monitored in turn.

In a system and process for monitoring the corrosion rate of different metals in identical corrosive fluids and under identical conditions, where a probe having three electrodes is employed of which one is a reference electrode, the electrodes should be employed in a triangular configuration, rather than in a linear configuration, to avoid erroneous results. However, a linear configuration of three electrodes may be successfully employed where the center electrode is a dedicated auxiliary electrode, the body of the probe is employed as the reference electrode, and the other two electrodes are test electrodes.

Various modifications can be made in the apparatus, circuitry and procedure by those skilled in the art in light of the above description without departing from the spirit of the invention as defined in the appended claims.

We claim:
1. A probe for use in measuring corrosion rates comprising:
   electrode holding means;
   a first rod-shaped metallic electrode held by said holding means and extending outwardly from and centrally positioned with respect to said holding means;
   at least three other rod-shaped metallic electrodes also held by said holding means and extending outwardly from said holding means, said other electrodes being arranged symmetrically in a circle around said first electrode, all said electrodes being parallel to each other, at least two of said other electrodes being made of different metals than each other and said first electrode;

means for insulating and sealing said electrodes in a fluid tight manner from said holding means;

electrical terminal means on said holding means comprising a single electrode terminal for each electrode; and conductive means on said holding means for electrically connecting each of said electrodes to a respective terminal in said terminal means, wherein said centrally positioned electrode is adapted to serve as a permanent auxiliary electrode, said other electrodes are test eectrodes and the holding means is adapted to serve as a reference electrode.

2. A probe as defined in claim 1 wherein said electrodes are cylindrical.

3. A probe as defined in claim 1 wherein at least one of said test electrodes is a galvanically coupled electrode comprising two dimensionally substantially identical metallic rods, said rods differing from each other in composition; conductive means electrically connecting said two rods and adapted to hold them in end to end relationship; and fluid tight sealing means positioned between said rods and at the end of said galvanically coupled electrode opposite said holding means.

4. A probe for use in measuring corrosion rates comprising.

electrode holding means;

a first rod-shaped metallic electrode held by said holding means and extending outwardly from and centrally positioned with respect to said holding means;

at least three other rod-shaped metallic electrodes also held by said holding means and extending outwardly from said holding means, said other electrodes being arranged symmetrically in a circle around said first electrode, all said electrodes being parallel to each other, at least two of said other electrodes being made of different metals than each other and said first electrode;

means for insulating and sealing said electrodes in a fluid tight manner from said holding means;

electrical terminal means on said holding means comprising a single electrode terminal for each electrode; and conductive means on said holding means for electrically connecting each of said electrodes to a respective terminal in said terminal means, wherein said centrally positioned electrode is adapted to serve as a reference electrode and each of said other electrodes is adapted to serve as a test electrode at a first time and as an auxiliary electrode at a second time.

5. The probe as defined in claim 4 further comprising circuit for connecting said probe to a single channel corrosion rate measuring instrument provided with reference, test and auxiliary electrode terminals, said circuit means comprising:

(a) first multiple pole switching means having a plurality of stationary poles and a common terminal mounting a movable contactor;

(b) conductive means for connecting said common terminal of said first switching means with said test electrode terminal of the measuring instrument;

(c) second multiple pole switching means having a plurality of stationary poles and a common terminal mounting a movable contactor;

(d) conductive means for connecting said common terminal of said second switching means with said auxiliary electrode terminal of the measuring instrument;

(e) conductive means including parallel branches for connecting each electrode terminal other than the reference electrode terminal to a pole of said first switching means and to a pole of said second switching means, each pole being connected to only a single electrode terminal;

(f) conductive means for connecting said reference electrode terminal with said reference electrode terminal of the measuring instrument; and (g) means for mechanically interlocking said first and second switching means so that said contactors move synchronously in a fixed sequence.

6. A probe as defined in claim 4 wherein at least one of said electrodes adapted to serve either as a test or an auxiliary electrode is a galvanically coupled electrode comprising two dimensionally substantially identical metallic rods, said rods differing from each other in composition; conductive means electrically connecting said two rods and adapted to hold them in end to end relationship; and fluid tight sealing means positioned between said rods and at the end of said galvanically coupled electrode opposite said holding means.

7. The probe as defined in claim 4 further adapted for use with a multiple channel corrosion measuring instrument, said probe further comprising circuit means for connecting said probe to the multiple channel corrosion rate measuring instrument, said circuit means including a plurality of instrument terminal means directly corresponding to the number of channels in the measuring instrument, each said instrument terminal means including terminals for connection to electrodes serving as reference, test and auxiliary electrodes, respectively, said circuit means comprising:

(a) conductive means including parallel branches connecting the reference electrode terminal with the reference electrode terminal in each instrument terminal means; and (b) conductive means including parallel branches connecting each electrode terminal other than the reference electrode terminal to a test electrode terminal in one instrument terminal means and an auxiliary electrode terminal in a different instrument terminal means, each terminal being connected to only a single electrode terminal.

8. A probe as defined in claim 4 wherein said electrodes are cylindrical.

* * * * *

UNITED STATES PATENT AND TRADEMARK OFFICE
CERTIFICATE OF CORRECTION

PATENT NO. : 4,667,150

DATED : May 19, 1987

INVENTOR(S) : Rudolph H. Hausler, Allen L. Savage and Jack B. Harrell, Jr.

It is certified that error appears in the above-identified patent and that said Letters Patent is hereby corrected as shown below:

At column 2, line 62, change "ciruict" to --circuit--.

At column 7, line 17, change "eectrodes" to --electrodes--.

Signed and Sealed this

Twenty-second Day of September, 1987

Attest:

DONALD J. QUIGG

Attesting Officer

Commissioner of Patents and Trademarks